United States Patent
Tokiwa et al.

(10) Patent No.: US 9,738,675 B2
(45) Date of Patent: Aug. 22, 2017

(54) WATER-SOLUBLE PHOTOCHROMIC COMPOUND

(71) Applicants: RIKKYO EDUCATIONAL CORPORATION, Tokyo (JP); JOSHO GAKUEN EDUCATIONAL FOUNDATION, Osaka (JP)

(72) Inventors: Hiroaki Tokiwa, Tokyo (JP); Masahiro Irie, Tokyo (JP); Kiyoshi Ikeda, Hiroshima (JP); Tadamune Otsubo, Hiroshima (JP)

(73) Assignees: RIKKYO EDUCATIONAL CORPORATION, Tokyo (JP); JOSHO GAKUEN EDUCATIONAL FOUNDATION, Osaka (JP)

( * ) Notice: Subject to any disclaimer, the term of this patent is extended or adjusted under 35 U.S.C. 154(b) by 70 days.

(21) Appl. No.: 14/427,635

(22) PCT Filed: Sep. 6, 2013

(86) PCT No.: PCT/JP2013/074052
§ 371 (c)(1),
(2) Date: May 5, 2015

(87) PCT Pub. No.: WO2014/042087
PCT Pub. Date: Mar. 20, 2014

(65) Prior Publication Data
US 2015/0307541 A1    Oct. 29, 2015

(30) Foreign Application Priority Data

Sep. 11, 2012   (JP) .................................. 2012-199292

(51) Int. Cl.
C07H 15/26 (2006.01)
C07D 333/38 (2006.01)
(Continued)

(52) U.S. Cl.
CPC ........... C07H 15/26 (2013.01); C07D 333/38 (2013.01); C07D 333/54 (2013.01); C07D 409/08 (2013.01); C09K 9/02 (2013.01)

(58) Field of Classification Search
CPC .... C07H 15/26; C07D 409/08; C07D 333/54; C07D 333/38; C09K 9/02
(Continued)

(56) References Cited

U.S. PATENT DOCUMENTS 7,101,497 B2 *  9/2006  Tanaka ................ C09K 9/02
                                                             106/499
2006/0079653 A1   4/2006  Dunaev et al.

FOREIGN PATENT DOCUMENTS

JP    2005-082507    3/2005
JP    2005-325087    11/2005
WO   2006/080647    8/2006

OTHER PUBLICATIONS

Tong et al, Tetrahedron letters, 2013, 54, 474-77.*
(Continued)

Primary Examiner — Ganapathy Krishnan
(74) Attorney, Agent, or Firm — Nixon & Vanderhye PC

(57) ABSTRACT

A diarylethene compound represented by formula (I)

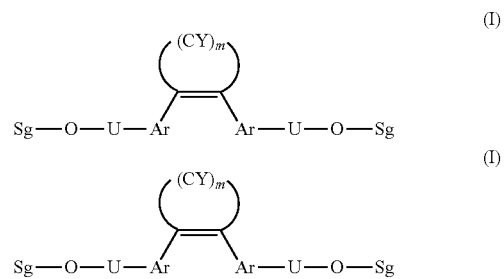

wherein, Sg is a monovalent sugar residue formed by removing one hydroxyl group from a sugar compound or a monovalent protected sugar residue formed by removing one hydroxyl group from a sugar compound in which one or more other hydroxyl groups are protected, and wherein the sugar is selected from the group consisting of a six-membered ring sugar, a five-membered ring sugar, cyclitol, and oligosaccharides containing a six-membered ring sugar, a five-membered ring sugar, or cyclitol;

U is $-(CH_2)_n-$, $-CH_2-U'-$, or $-C(=O)-$
wherein
n is an integer of 1 to 5,
U' is a C2-C10 branched alkylene group binding to Ar); and Ar is a group represented by formula (A1) or (A2);

(Continued)

-continued

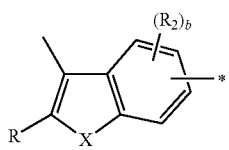
(A2)

wherein,
X is S, SO$_2$, NR$_3$ in which R$_3$ is a C1-C3 alkyl group, or O,
R is C1-C4 alkyl group,
R$_1$ and R$_2$ are independently a C1-C3 alkyl group,
a is 0 or 1,
b is an integer of 0-3, and
* represents a bond with U;
Y is a hydrogen atom or a halogen atom; and
m is an integer of 3 to 5.

9 Claims, 3 Drawing Sheets

(51) Int. Cl.
C07D 333/54 (2006.01)
C09K 9/02 (2006.01)
C07D 409/08 (2006.01)

(58) Field of Classification Search
USPC .................................. 536/18.1; 549/53, 59
See application file for complete search history.

(56) References Cited

OTHER PUBLICATIONS

Barachevsky et al, Russian chemical Bulletin, Intl. Edn., 2008, 57(4), 867-75.*

Norberg, T., Chapter 4, pp. 87 and 91 in Modern Methods in Carbohydrate Synthesis, Ed. by Shaheer Khan and Roger O'Neill, Harwood Academic publishers, 1996.*

Ayt et al. "Masking photochromic films for nanolithography technology" Physica Status Solidi C, vol. 8, No. 9, pp. 2866-2869 (Sep. 2011).

Hirose et al. "Temperature-light dual control of clouding behavior of an oligo(ethylene glycol)-diarylethene hybrid system" Advanced Materials, vol. 20, No. 11, pp. 2137-2141 (Jun. 2008).

Irie et al. "Organic chemistry: A digital fluorescent molecular photoswitch" Nature, vol. 420, No. 6917, pp. 759-760, abstract only (Dec. 2002).

Jones & Senft "An improved method to determine cell viability by simultaneous staining with fluorescein diacetate-propidium iodide" Journal of Histochemistry and Cytochemistry, vol. 33, No. 1, pp. 77-79 (Jan. 1985).

Kawai "Photochromic bis(monoaza-crown ether)s. Alkali-metal cation complexing properties of novel diarylethenes" Tetrahedron Letters, vol. 39, No. 25, pp. 4445-4448 (Jun. 1998).

Kobatake et al. "Photochromism of 1,2-bis(2,5-dimethyl-3-thienyl)perfluorocyclopentene in a single crystalline phase" Journal of the American Chemical Society, vol. 121, No. 11, pp. 2380-2386 (Mar. 1999).

Li et al. "Synthesis and characterization of light-driven dithienylcyclopentene switches with axial chirality" Journal of Organic Chemistry, vol. 76, No. 17, pp. 7148-7156 (Sep. 2011).

Matsuda et al. "Very high cyclization quantum yields of diarylethene having two N-methylpyridinium ions" Chemistry Letters, vol. 32, No. 12, pp. 1178-1179, abstract only (Jan. 2003).

Polyakova et al. "Synthesis of photochromic compounds for aqueous solutions and focusable light" European Journal of Organic Chemistry, vol. 2011, No. 18, pp. 3301-3312 (Jun. 2011).

Takeshita et al. "Photochromism of dithienylethenes included in cyclodextrins" Journal of Organic Chemistry, vol. 63, No. 25, pp. 9306-9313 (Nov. 1998).

Yamaguchi & Irie "Photochromism of bis(2-alkyl-1-benzothiophen-3-yl)perfluorocyclopentene derivatives" Journal of Photochemistry and Photobiology A: Chemistry, vol. 178, Nos. 2-3, pp. 162-169 (Mar. 2006).

Int'l Search Report for PCT/JP2013/074052, eight pages (dated Nov. 2013).

Written Opinion of ISA for PCT/JP2013/074052, 11 pages (dated Nov. 2013).

Shoji et al. "Photochromic diarylethene derivatives bearing hydrophilic substituents" Israel Journal of Chemistry, vol. 53, No. 5, pp. 303-311 (May 2013).

Uchida et al. "An optically active diarylethene having cholesterol units: A dopant for photoswitching of liquid crystal phases" Chemistry Letters, vol. 29, No. 6, pp. 654-655 (Jun. 2000).

EPO supplementary search report for related EP 13837714.8, four pages, dated Mar. 11, 2016.

* cited by examiner (a)            (b)

(a)        (b)        (c)

WATER-SOLUBLE PHOTOCHROMIC COMPOUND

This is the U.S. national stage under 35 U.S.C. 371 of International Application No. PCT/JP2013/074052, filed Sep. 6, 2013; which claims priority to JP Application No. 2012/199292, filed Sep. 11, 2012; the entire contents of each of which are hereby incorporated by reference.

TECHNICAL FIELD

The present invention relates to a water-soluble photochromic molecule, and more specifically to a water-soluble diarylethene compound.

BACKGROUND ART

Photochromic molecules are molecules that reversibly transform between two isomers with different absorption spectra while maintaining the same molecular weight when irradiated with appropriate wavelength of light. The diarylethene compound is known to exhibit excellent photochromic performance (Non-Patent Document 1). The diarylethene has a following structure, and it undergoes cyclization/cycoreversion reactions upon irradiation with light as shown in the following scheme.

[Formula 1]

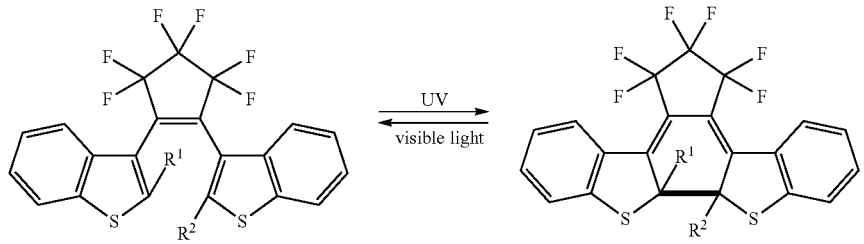

Extensive studies have been carried out to apply the photochromic molecules as optical memory media that can optically store information (Patent Document 1, etc.). In such use, the media were prepared by dissolving photochromic molecules in an organic solvent, then spreading the resulting solution over a substrate.

Recently, bioimaging using fluorescent microscope, which is a method to observe an image by binding fluorochrome molecules to biomolecules, has been actively studied. Bioimaging that employs green fluorescent proteins (GFP) is frequently used, but this method is disadvantageous in that the label molecule is large, and the protein-protein interaction affects the target biomolecule. Diarylethenes are expected to achieve bioimaging with high resolution, since they are low molecular weight compounds. However, it is indispensable to provide water-solubility to the compounds for the application to biological samples.

In the studies of optical memory media mentioned above, the diarylethene compound did not need to be dissolved in water, so Patent Document 1 does not mention anything about a water-soluble diarylethene compound. Concerning water-solubility, Non-Patent Documents 3, 4 teach diarylethene compounds that have ionic groups or amphiphilic groups. However, these compounds tend to be aggregated in water, and would excessively affect the target molecule due to their strong ionic interaction, so they are hardly applied to bioimaging. Under such situation, a highly water-soluble diarylethene compound obtained by a different means was desired.

CITATION LIST

Patent Documents

Patent Document 1: Japanese Publication No. 2005-325087

Non-Patent Documents

Non-Patent Document 1: M. Irie et al., Nature, 420, 759 (2002)
Non-Patent Document 2: K. H. Jones and J. A. Senft, J. Histochem. Cytochem., 33, 77 (1985)
Non-Patent Document 3: M. Takeshita, et al., J. Org. Chem., 63, 9306 (1998)
Non-Patent Document 4: M. Matsuda, et al., Chem. Lett. 32, 1178 (2003)
Non-Patent Document 5: S. Kobatake, et al., J. Am. Chem. Soc. 121, 2380 (1999)
Non-Patent Document 6: T. Yamaguchi, et al., J. Photochem. Photobio. A, 178, 162 (2006)

SUMMARY OF INVENTION

Technical Problem

In view of the above situation, the object of the present invention is to provide a highly water-soluble diarylethene compound.

Solution to Problem

The present inventors found that a diarylethene compound having sugar groups has good water-solubility, and completed the present invention. In other words, the above object is achieved by the present inventions shown below.

[1] A diarylethene compound represented by the following formula (I).

[2] A method for producing the diarylethene compound of [1] above comprising:
(1) a step of preparing a halogenated sugar derivative that is derived from a sugar-type compound selected from a group consisting of a six-membered ring sugar, a five-membered ring sugar, cyclitol and oligosaccharides containing a six-membered ring sugar, a five-membered ring sugar, or cyclitol, and that includes 1 hydroxyl group substituted with a halogen atom and all other hydroxyl groups protected by protection groups;

(2) an etherification step of reacting the halogenated sugar derivative with the compound represented by formula (a) to generate a compound represented by formula (b); and
(3) a deprotection step of removing the protection group of a compound represented by formula (b).

Advantageous Effects of Invention

The present invention can provide a diarylethene compound having a high water-solubility.

DESCRIPTION OF EMBODIMENTS

Figure 1:
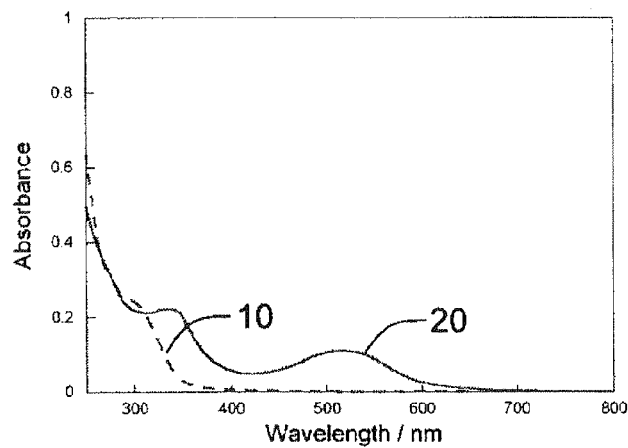
FIG. 1 is a diagram showing the photochromic property of an aqueous solution of a compound of Example 1.

1. Diarylethene Compound
The diarylethene compound of the present invention is represented by formula (I).

[Formula 2]

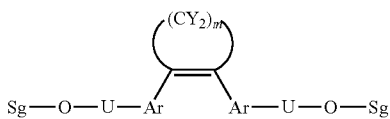

(1) Sugar-Type Residue Sg
The compound has sugar-type residues Sg. Sugar-type residue is a group derived from sugar or a similar compound. Sg is a monovalent sugar-type residue consisting of a sugar-type compound excluding one hydroxyl group, the sugar-type compound being selected from a group consisting of a six-membered ring sugar, a five-membered ring sugar, cyclitol and oligosaccharides containing a six-membered ring sugar, a five-membered ring sugar, or cyclitol. Some of the hydroxyls in the sugar-type residue may be protected by protection groups. The sugar-type compound is referred to hereinafter as simply "sugar" and the sugar-type residue is referred to hereinafter as simply "sugar residue" for convenience.
A six-membered ring sugar is sugar with 6-membered ring structure, including glucopyranose, arabinopyranose, xylopyranose, lyxopyranose, allopyranose, altropyranose, mannopyranose, gulopyranose, idopyranose, galactopyranose, talopyranose, and glucuronic acid, without being limited thereby.
A five-membered ring sugar is sugar with 5-membered ring structure, including ribofuranose, arabinofuranose, xylofuranose, erythrofuranose, threofuranose, and lyxofuranose, without being limited thereby.

Cyclitol is a cycloalkane polyol (polyhydroxy cycloalkane), that is, a cyclic sugar alcohol, and it includes inositol as an example.
An oligosaccharide is a compound composed of about 2 to 15 units of compounds that are a six-membered ring sugar, a five-membered ring sugar, and a cyclitol sugar bound to each other by the glycoside linkage, etc. Examples of oligosaccharides include sucrose, raffinose, stachyose, trehalose, lactose, etc., without being limited thereby.
When availability is considered, a preferable sugar in the present invention is glucopyranose.
Sg is a monovalent sugar residue excluding a hydroxyl group from the above sugars. Any hydroxyl group can be removed, but a hydroxyl group bound to a carbon atom in the ring is preferable, and a hydroxyl group on the position-1 carbon atom (hemiacetal hydroxyl group) is more preferable. For example, a sugar residue of glucopyranose excluding the hemiacetal hydroxyl group is a glucosyl group, and it is represented by the following chemical formula.

[Formula 3]

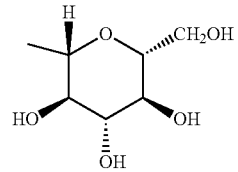

A glucosyl group may be either an α-glucosyl group, or a β-glucosyl group, but the β-glucosyl group is preferable from the viewpoint of reducing the steric hindrance.
Also, as mentioned above, some of the hydroxyl groups can be protected in the sugar residue. A more detailed explanation of the protection group will follow, but an acyl group, such as an acetyl group, is preferable. If there is a protection group, it should preferably exist in a number of 1 to 2, and more preferably 1 per 1 sugar residue.
(2) Aromatic Group Ar
Ar is an aromatic group represented by the following formula (A1) or (A2).

[Formula 4]

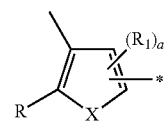

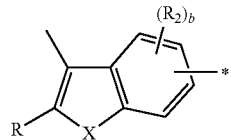

X is S, $SO_2$, $NR_3$ ($R_3$ is a C1-C3 alkyl group), or O, of which S or $SO_2$ is preferable to obtain a good photochromic property. In particular, S is preferable as X in formula (A1), and S or $SO_2$ is preferable as X in formula (A2).
R is a C1-C4 alkyl group. In the present invention, the alkyl group includes chain-shaped and a branch-shaped groups. Hence, C1-C4 alkyl group is specifically a methyl group, an ethyl group, an n-propyl group, an i-propyl group, an n-butyl group, and a t-butyl group.

$R_1$, $R_2$ are independently C1-C3 alkyl groups. When we say "independently," it means that $R_1$, $R_2$ can be the same or they may differ. $R_1$ is a substituent at position-4 or position-5 of a 5 membered-ring in formula (A1). a is the number of $R_1$, which is either 0 or 1. The presence of $R_1$ may reduce the photochromic property, so $R_1$ should preferably not exist (i.e. a=0), but if it does exist, a less bulky $R_1$ provides a better photochromic property, so $R_1$ should preferably be a methyl group.

$R_2$ is a C1-C3 alkyl group, and it is a substituent at positions 4 to 7 of the heterocyclic ring in formula (A2). b is the number of $R_2$s, which is an integer between 0 to 3. The presence of $R_2$ may reduce the photochromic property, so $R_2$ should preferably not exist (i.e. b=0), but if it does exist, b should preferably be 1 or 2, of which 1 is more preferable. If $R_2$ does exist, $R_2$ should preferably be a methyl group for the reason provided above.

In formula (A1), * indicates a linkage of the 5-membered ring with the linkage group U. To reduce the steric hindrance, the position-5 carbon atom of the 5 membered-ring should bind with U. If there is an $R_1$, it will bind to position-4. Similarly in formula (A2), * indicates a linkage of the benzene ring with the linkage group U. To reduce the steric hindrance, the position-6 carbon atom should bind with U.

(3) Linkage Group U

U is a linkage group to link Sg and Ar, and it is —$(CH_2)n$- , —$CH_2$—U'—, or —C(=O)—. n is an integer of 1 to 5. A large n may reduce the water-solubility of the diarylethene compound to be obtained, so n should preferably be 1 to 3, and more preferably 1.

U' is a C1-C10 alkyl group binding with Ar. The water-solubility of diarylethene compound may decrease for a large number of carbons, so the number of carbons should preferably be 1 or 2, and more preferably 1. As mentioned above, the alkyl group includes chain-shaped and branch-shaped groups.

(4) Ethene Unit

The —$(CY_2)_m$— in formula (I) shows that the compound has an alicyclic structure. Y is a hydrogen atom or a halogen atom. To obtain a good photochromic property, Y should preferably be a halogen atom, and more preferably a fluorine atom. m is an integer of 3 to 5 and it should preferably be 5 for the same reason.

2. Production Method

The diarylethene compound of the present invention is produced by any given method, but a preferable production method is provided below.

2-1. First Production Method

The present method includes:

(1) a step of preparing a halogenated sugar derivative that is derived from a sugar-type compound selected from a group consisting of a six-membered ring sugar, a five-membered ring sugar, cyclitol and oligosaccharides containing a six-membered ring sugar, a five-membered ring sugar, or cyclitol, and that includes 1 hydroxyl group substituted with a halogen atom, and all other hydroxyl groups protected by protection groups;

(2) an etherification step of reacting the halogenated sugar derivative with the compound represented by formula (a) to produce a compound represented by formula (b);

(3) a deprotection step of removing the protection group of a compound represented by formula (b).

[Formula 5]

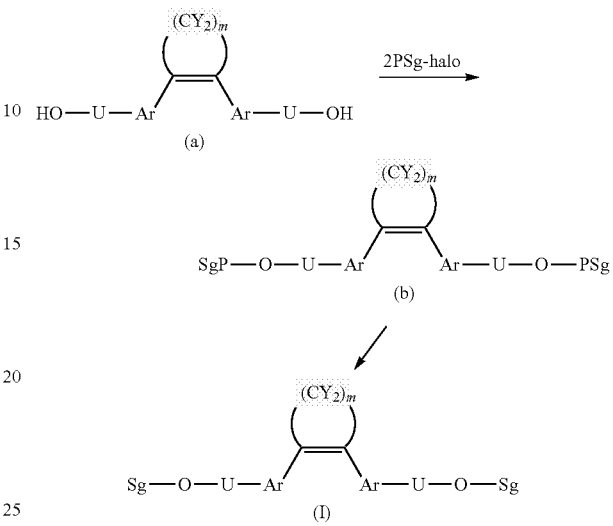

A detailed explanation is provided below, and for the ease of understanding, an example will be provided in which the halogenated sugar derivative is acyl halogenated sugar, and the etherification step includes a glycosylation reaction.

(1) Preparation Step of Acyl Halogenated Sugar (Preparation Step of Halogenated Sugar Derivative)

The acyl halogenated sugar used in the present invention is derived from a sugar selected from a group consisting of a six-membered ring sugar, a five-membered ring sugar, cyclitol and oligosaccharides containing a six-membered ring sugar, a five-membered ring sugar, or cyclitol, and it includes 1 hydroxyl group substituted with a halogen atom, and all other hydroxyl groups protected by protection groups. In the above scheme, the acyl halogenated sugar is represented by PSg-halo. The hydroxyl group substituting the halogen atom should preferably be the hydroxyl group on the anomer position.

A protection group is a group for protecting the hydroxyl group to prevent side reaction of the hydroxyl group in the sugar. In the present invention, the hydroxyl group can be protected by a group that is commonly used. Examples of such protection group includes an acyl group, an acetal group, and a silyl ether group. Among these, the acyl group is preferable since it is easy to deprotect, and an acetyl group is more preferable.

The acyl halogenated sugar can be prepared by a known method. For example, it can be produced by reacting pentaacetyl glucopyranose with HOAc-HBr (hydrogen bromide-acetic acid solution). The hydroxyl group on the anomer position (a hydroxyl group on the position-1 carbon atom) is normally halogenated. The above step can be performed by dissolving the protected sugar in a hydrogen bromide-acetic acid solution, then sealing it and reacting it for a day and a night. A preferable acyl halogenated sugar is represented by formula (s1) below.

[Formula 6]

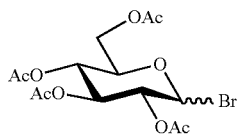
(s1)

(2) Glycosylation Step (Etherification Step)
1) Diols Represented by Formula (a)
This step is a reaction of the acyl halogenated sugar and diols represented by formula (a).

[Formula 7]

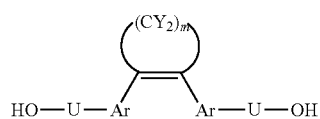
(a)

In formula (a), U, Ar, Y and m are as defined above. However, U in the present production method should preferably be —$(CH_2)_n$— or —$CH_2$—U'—.

The diol can be prepared by a known method. For example, a —U—OH group may be introduced in the aromatic group Ar of the diarylethenc compound of formula (j) shown in the following scheme.

[Formula 8]

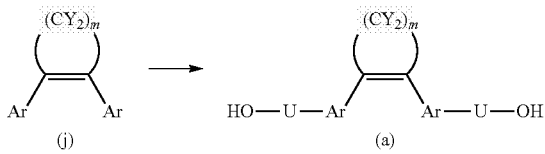

Specifically, the diarylethene compound of formula (j) and dichloromethylmethyl ether are reacted under the presence of $AlCl_3$, etc. to introduce a formyl group in the Ar group, and a reduction of the formyl group will provide a diol in which —$CH_2$—OH is introduced as the —U—O group.

The diarylethene compound of formula (j) whose Ar is a thiophene structure is described in, for example, Non-Patent Document 5. The compound whose Ar is a benzothiophene structure is descried in, for example, Non-Patent Document 6.

2) Intermediate Represented by Formula (b)
A reaction of the diol of formula (a) and an acyl halogenated sugar induces a glycosylation reaction that generates an intermediate represented by formula (b).

[Formula 9]

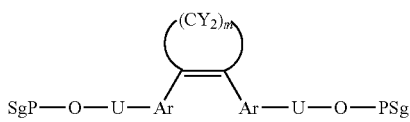
(b)

In formula (b), U, Ar, Y and m are as defined above. PSg is a sugar residue of the Sg in which all hydroxyl groups are protected.

This reaction occurs by the detachment of a hydrogen atom of the compound of formula (a) and a halogen at the anomer position of the acyl halogenated sugar, so it should preferably be performed under the presence of a reaction accelerator that accelerates the detachment of the hydrogen atom and halogen. Examples of the reaction accelerator include silver oxide, such as $Ag_2O$, and mercury salts, such as $HgBr_2$, $Hg(CN)_2$. In the present invention, it is preferable to use $Ag_2O$, since it is more capable of accelerating reaction. The amount of $Ag_2O$ to be used should preferably be 5 to 10 mols against 1 mol of a compound of formula (a).

In addition, the reaction can be further accelerated by also using a dehydrator. A known dehydrator can be used, but a dehydrator that can be easily removed, such as a molecular sieve, etc., is preferable. The amount of molecular sieve 4 Å to be used should preferably be 0.10 g/2 mL of the solvent.

The solvent to be used in the present step is not limited, but a solvent having low solubility to water is preferable, since removing water from the system further accelerates the reaction as mentioned above. An example of a preferable solvent includes a chlorine-type hydrocarbon, such as methylene chloride, and an aromatic hydrocarbon, such as toluene. In particular, a chlorine-type hydrocarbon is more preferable.

The reaction temperature is determined as necessary from the viewpoint of accelerating reaction and regulating side reaction. A temperature between 10 to 40° C. is preferable in the present invention.

As mentioned above, it is preferable to use an acyl halogenated sugar that includes a halogenated hydroxyl group on the position-1 carbon atom and other hydroxyl groups protected for ease of synthesis or other reasons, but such acyl halogenated sugar has an α-isomer and a β-isomer. In the acyl halogenated sugar, the neighboring hydroxyl group on position-2 is protected by an acyl group, and the neighboring-group participation brings about a preferential generation of β-glycosyl isomer. So when the above acyl halogenated sugar of formula (s1) is used to obtain the compound of formula (a), the PSg in the obtained compound is a group derived from the β-glycosyl group.

(3) Deprotection Step
This step removes the protection group of the intermediate represented by formula (b). The protection group can be removed by a known method. For example, when the hydroxyl group is protected by an acyl group, such as an acetyl group, the protection group can be readily removed by reacting the protected hydroxyl group with alkali, such as lithium hydroxide, sodium hydroxide, potassium carbonate. It is preferable to use lithium hydroxide in the present invention, and it is more preferable for the amount of use to be 5 to 10 mol against 1 mol of the intermediate represented by formula (b).

The solvent to be used in the present reaction is not limited, but alcohol such as methanol is preferable. The reaction temperature is not limited, but a temperature of 10 to 30° C. is preferable.

2-2. Second Production Method
The method comprises:
(1) a step of preparing a protected sugar compound selected from a group consisting of a six-membered ring sugar, a five-membered ring sugar, cyclitol and oligosaccharides containing a six-membered ring sugar, a five-membered ring sugar, or cyclitol, and all hydroxyl groups excluding one are protected by protection groups;

(2) an etherification step of reacting the protected sugar compound with the compound represented by formula (p) to generate a compound represented by formula (q);

(3) a deprotection step of removing the protection group of a compound represented by formula (p).

The protected sugar compound is referred to hereinafter simply as "protected sugar" for the reason mentioned above. The scheme of the method is shown below.

[Formula 10]

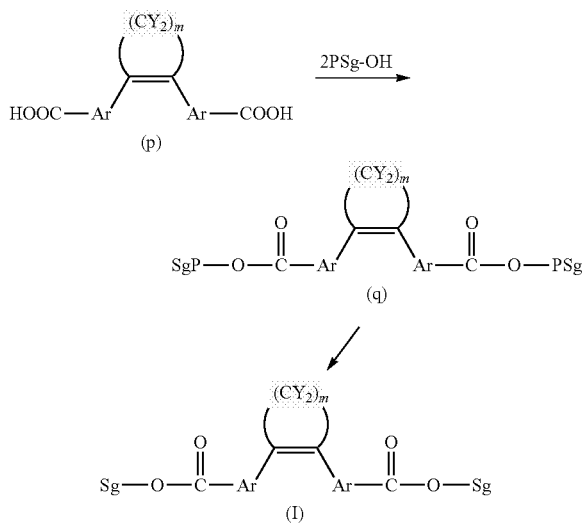

(1) Preparation Step of Protected Sugar

The protected sugar is shown as PSg-OH in the scheme. The protected sugar is a sugar that has all of its hydroxyl groups excluding one protected by protection groups. Those protection groups mentioned above can be used, but the group preferable in the present production method is the acetal group, and a more preferable group is the methoxymethyl group.

The protected sugar can be prepared by a known method. For example, it can be produced by introducing a protection group in sugar, such as furanose. All hydroxyl groups excluding the hydroxyl group on the anomer position (a hydroxyl group on the position-1 carbon atom) should preferably be protected.

Protected sugars preferable for use in the present invention include the compound represented by formula (s2) below. In formula (s2), R' is a methyl group or an ethyl group, and the methyl group is preferable, since it can easily be deprotected.

[Formula 11]

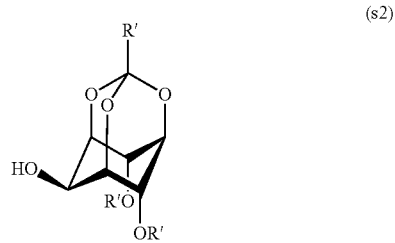

(2) Esterification Step

1) Dicarboxylic Acids Represented by Formula (p)

This step performs a reaction of a protected sugar and dicarboxylic acids represented by formula (p). In formula (p), Ar, Y and m are defined as shown above. The dicarboxylic acids can be prepared by a known method. For example, a dicarboxylic acid of formula (p) can be produced by introducing a formyl group to the aromatic group Ar of the diarylethene compound of formula (j) to obtain a diformyl, then oxidating the formyl group to produce a dicarboxylic acid of formula (p), as indicated in the first production method.

2) Intermediate Represented by Formula (q)

A reaction of the dicarboxylic acids of formula (p) and protected sugar generates intermediates represented by formula (q). In formula (q), Ar, Y, m and PSg are defined as shown above. The reaction is an esterification reaction, so it should be carried out under the presence of a known reaction accelerator. Examples of the reaction accelerator include a dehydrator, such as DCC. The amount of DCC to be used should preferably be 2 to 5 mols against 1 mol of the compound of formula (p).

The solvent to be used in the present step is not limited, but a removal of water from the system accelerates reaction as mentioned above, so a solvent having low water-solubility is preferable. The preferable solvents are as already mentioned above.

The reaction temperature is determined as necessary from the viewpoint of accelerating reaction and regulating side reaction. A temperature between 10 to 40° C. is preferable in the present invention.

(3) Deprotection Step

This step removes the protection group of the intermediate of formula (q). The protection group can be removed by a known method. For example, when the protection group is an acetal group, deprotection can be carried out by an excessive amount of acid, such as chloride. The solvent to be used in the present reaction is not limited, but alcohol, such as methanol, is preferable. The reaction temperature should preferably be 10 to 30° C. without being limited thereby.

As a result of the above steps, the target compound can be obtained. The obtained compound is represented by formula (I) and has a linking group U of —C(=O)—.

3. Usages and the Like

The diarylethene compound of the present invention is soluble in water or an aqueous solvent. In other words, in the present invention, the compound is water-soluble if it dissolves in water or in a water/organic solvent (mixed solvent) having water concentration of 70 wt % or higher, preferably 80 wt % or higher, and more preferably 90 wt % or higher.

Further, the diarylethene compound of the present invention contains sugar residues, so the sugar residues can be further modified to introduce labeling groups or enhance biocompatibility. Accordingly, the diarylethene compound of the present invention can be readily incorporated into biological sample to achieve bioimaging at a high resolution.

In addition, the diarylethene compound of the present invention can achieve high resolution bioimaging when used for super-resolution microscopy (PALM/STORM). Specifically, in a biological sample incorporating a diarylethene compound, the ON (open-ring) molecules can be turned to OFF (close-ring) state by irradiation with different light, then a small number of molecules can be turned on by irradiation with UV light again for observation, and repetition of this process allows the position of the independent molecules to be detected and an image with higher resolution to be obtained.

EXAMPLES

Example 1-1

Synthesis of Thiophene Compound 5

The reaction scheme is shown below.

[Formula 12]

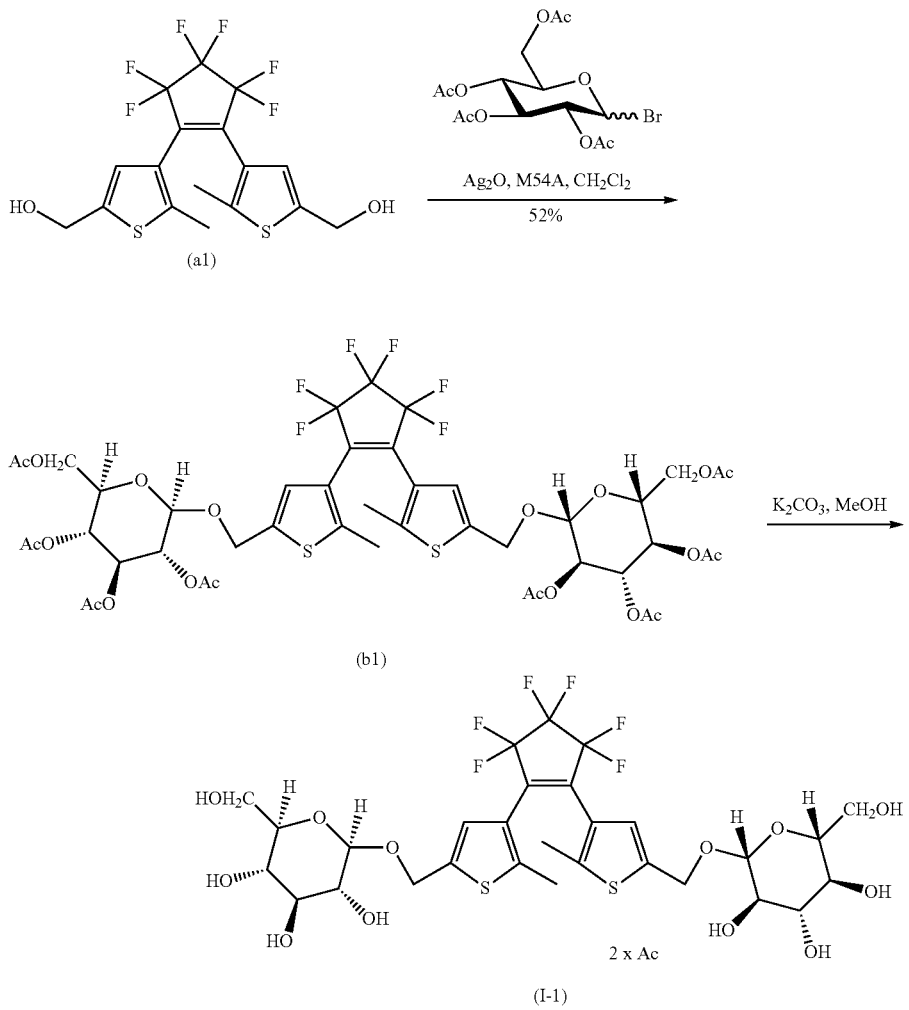

(a1)

(b1)

(I-1)

1) Synthesis of Acyl Halogenated Sugar

A compound (bromotetraacetoglucose) composed of glucopyranose having the hydroxyl group on the position-1 carbon atom substituted with Br, and having all other hydroxyl groups protected with acetyl groups, was prepared as an acyl halogenated sugar. Specifically, the compound was synthesized in the following manner. Pentaacetyl glucopyranose (TCI) was dissolved in an excessive amount of hydrogen bromide-acetic acid solution (hydrogen bromide: acetic acid=1:1 (mol rate)), then, it was sealed and reacted for a day and a night at room temperature to quantitatively obtain bromotetraacetoglucose.

2) Synthesis of Diols of Formula (a1)

The compound is a diol in which linking group U (methylene group) binds to position-5 of the thiophene ring. The diol was prepared by the following reaction.

[Formula 13]

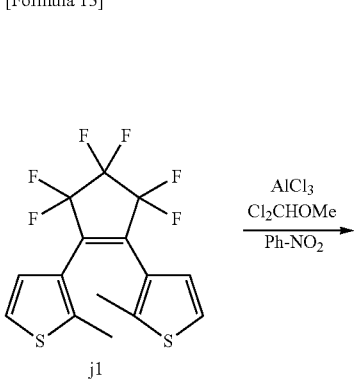

j1

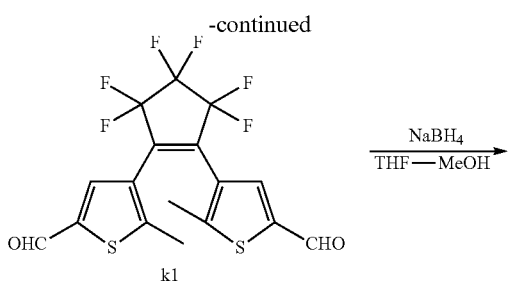

k1

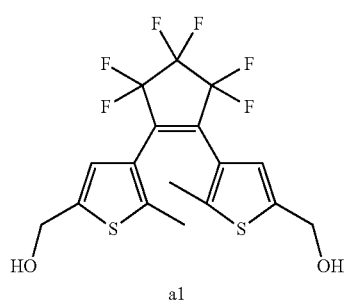

a1

The method of Non-Patent Document 5 was used to prepare a compound of formula (j1), then the compound was used to obtain a diformyl of formula (k1). NaBH$_4$ (51 mg, 2 eq.) was added to the THF-MeOH (3 mL/3 mL) solution of the diformyl (667 μmol) at 0° C. in two separate instances, then the solution was agitated at 0° C. for 4 hours. The reaction solution was diluted with ethyl acetate, then the organic layer was washed with water (3 times) and with saturated saline solution (once) in that sequence, and dried with sodium sulfuric acid. The drying agent was filtered out and the solvent was decompressed/removed, then the residue was refined by column chromatography (hexane:ethyl acetate=2:1) to obtain a diol of formula (a1).

3) Synthesis of Intermediate Represented by Formula (b1)

The diol of formula (a1) (69 mg, 0.16 mmol) and bromotetraacetoglucose (197 mg, 0.48 mmol) were dissolved in CH$_2$Cl$_2$ (3 mL), and 0.2 g of molecular sieve 4 Å (by NACALAI TESQUE, INC.) was added to the mixture to be agitated for 1 hour at room temperature. Ag$_2$O (111 mg, 0.48 mmol) was further added under an argon airflow at room temperature with the light blocked, then the mixture was agitated for 24 hours. After the reaction ended, the un-dissolved matter was filtered out under reduced pressure, the filtrate was decompressed/concentrated, and the residue was separated/refined by silica gel column chromatography (hexane:ethyl acetate=2:1 to 1:1) to obtain an intermediate represented by formula (b1) (96 mg, yield 52%).

The intermediate was analyzed using a mass analysis device (Model No. JMS-T100LC, by JEOL Ltd) and a peak of [M+Na]$^+$=1111 was obtained. The analysis was measured by the ESI positive mode, so the result included the target and Na (atomic weight 23) derived from the solvent or glass. Hence, the peak is a result of the target mass 1088, indicating that the obtained compound is a compound of formula (b1).

ESI-MS m/z: 1111 [M+Na]$^+$.

HR-ESI-MS m/z: 1111.21787 [M+Na]$^+$ (Calcd for C$_{45}$H$_{50}$F$_6$NaO$_{20}$S$_2$, 1111.21387).

4) Synthesis of the Compound of Formula (I-1) (Target Compound)

A compound represented by formula (b1) (38 mg, 0.03 mmol) and 2 mL of methanol were introduced into a three neck flask and agitated to form a homogenous solution. Potassium carbonate (13 mg, 0.3 mmol) was introduced into the flask, and a reaction was performed at room temperature for 15 hours. The reaction mixture was subjected to gel filtration/refinement by Bio-Gel P-2 Gel (by Bio-Rad) to obtain a compound of formula (I-1) in which 2 hydroxyl groups are protected by acetyl groups. The yield of the deprotection reaction was 56%.

5) Assessment of Water-Solubility

When an aqueous solution incorporating a small amount (50 μL) of methanol was prepared, and 2.5 mg of the compound of formula (I-1) was added to the solution, a reddish violet solution was obtained, indicating that the compound was dissolved. Likewise, when the compound of formula (I-1) was dissolved in water that does not contain methanol, a reddish violet solution was obtained, indicating that the compound was dissolved. In addition, the compound (I-1) was dissolved in a small amount of methanol, to which distilled water (4 mL) was added to prepare a 95% aqueous solution, and hence, an absorption spectrum of FIG. 1 (by Hitachi, using U-4100) was obtained. The spectrum of the open ring form is shown by dotted line 10. Irradiation with the UV light (313 nm) turned the solution purple, and a spectrum shown by solid line 20 was observed.

Example 1-2

Synthesis of a Thiophene Compound

A compound of formula (I-1) was produced similarly to Example 1-1, except for using lithium hydroxide instead of potassium carbonate (5 mol equivalent against diaryl ethene). A compound of formula (I-1) having 2 hydroxyl groups protected by acetyl groups was obtained as a result. The obtained compound included 2 acetyl groups. The yield in the deprotection reaction was 56%.

Example 2
Synthesis of Benzothiophene Sulfone
The reaction scheme is shown below.
[Formula 14]
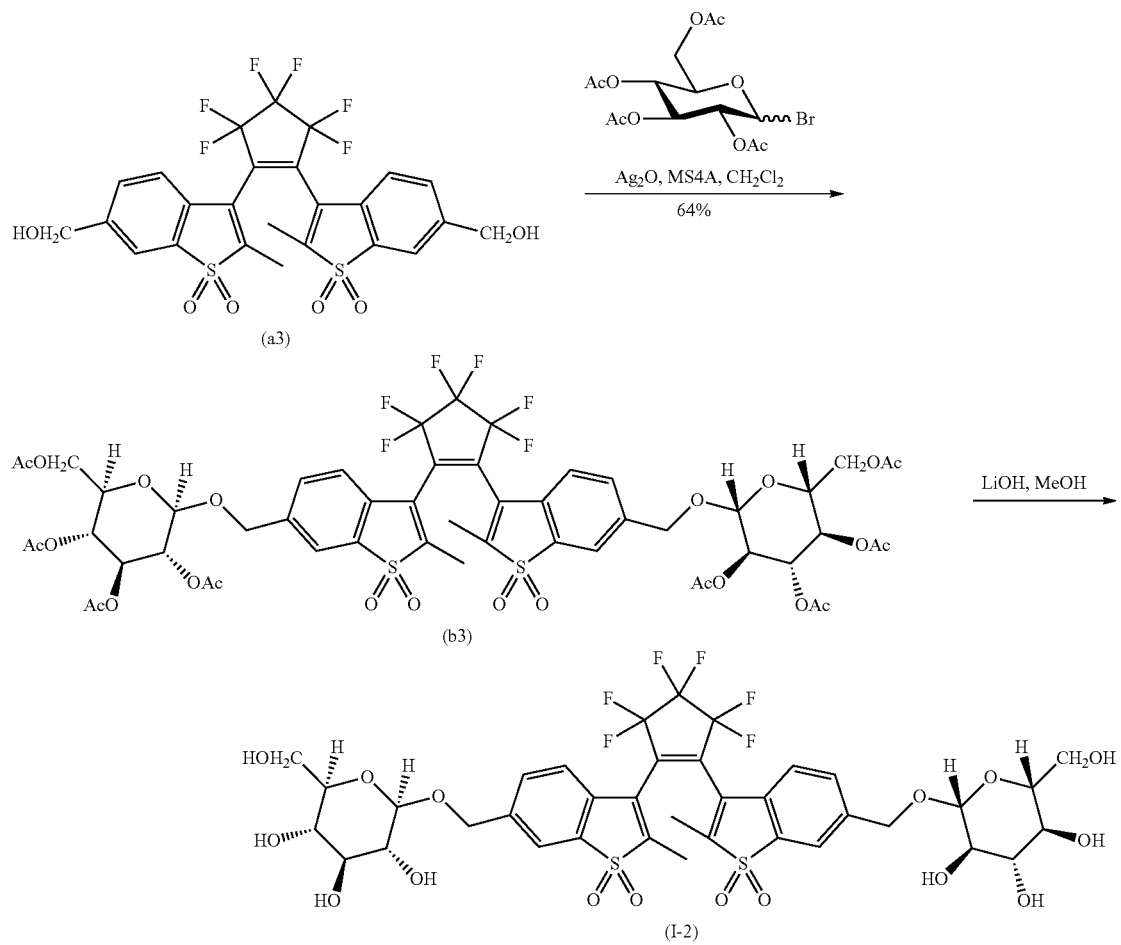
1) Synthesis of Diols of Formula (a2)
The compound is a diol including benzothiophene rings binding to linkage groups U (methylene group) at position-6. The diol was prepared by the following reaction.
[Formula 15]
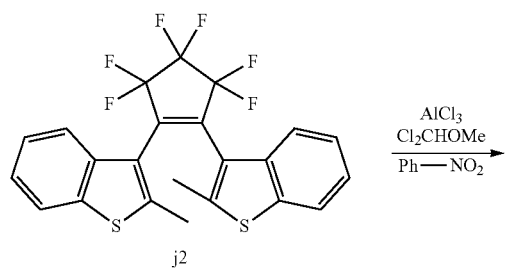
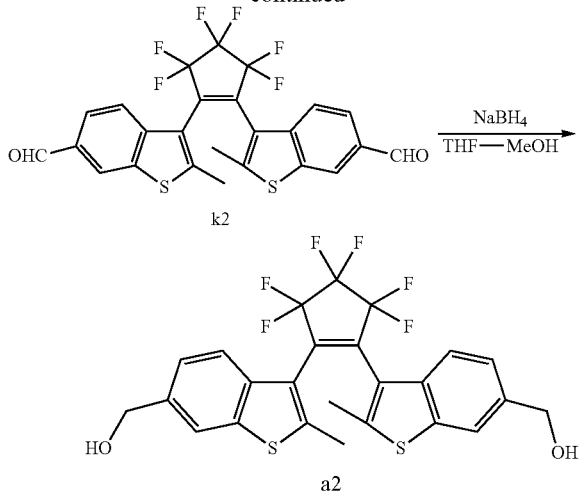

A compound of formula (j2) prepared by the method of Non-Patent Document 6 was formylated to obtain a diformyl of formula (k2).

NaBH$_4$ (51 mg, 2 eq.) was added to the THF-MeOH (3 mL/3 mL) solution of the diformyl (350 mg, 667 μmol) at 0° C. in two separate instances, then the solution was agitated at 0° C. for 4 hours. The reaction solution was diluted with ethyl acetate, then the organic layer was washed with water (3 times) and with saturated saline solution (once) in that sequence, and dried with sodium sulfuric acid. A drying agent was filtered out and the solvent was decompressed/removed, and the residue was refined by column chromatography (hexane:ethyl acetate=2:1) to obtain a diol of formula (a2) (220 mg, 62% yield) as a pale red amorphous. The mass analysis result of the compound was as shown below.

ESI-MS m/z: 551 [M+Na]$^+$.

HR-ESI-MS m/z: 551.05427 [M+Na]$^+$ (Calcd for C$_{25}$H$_{18}$F$_6$NaO$_2$S$_2$, 551.05501).

2) Synthesis of Diols of Formula (a3)

The compound was prepared by the following reaction.

[Formula 16]

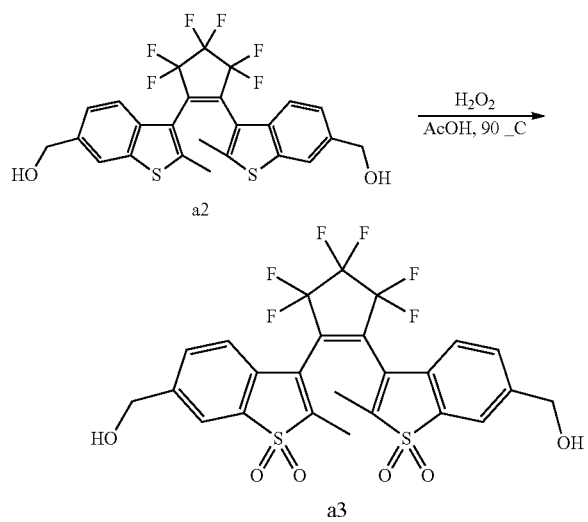

Acetic acid (2.5 mL) was added to the diol of a2 (50 mg, 95 μmol), and the mixture was heated to dissolve the diol. Hydrogen peroxide solution (35%, 370 μL) was added to the reaction solution and agitated at 90° C. for 2 hours. After cooling, the reaction solution was diluted with ethyl acetate, then the organic layer was washed with water (3 times) and with saturated saline solution (once) in that sequence, and dried with sodium sulfuric acid. A drying agent was filtered out and the solvent was decompressed/removed, and the residue was refined by column chromatography (hexane:ethyl acetate=2:1 to 1:1) to obtain a diol (39 mg, 70% yield) of formula (a3) and a monoacetyl (6.9 mg, 12% yield) each as a pale yellow amorphous. The mass analysis result of the diol of formula (a3) was as shown below.

ESI-MS m/z: 615 [M+Na]$^+$.

HR-ESI-MS m/z: 615.03291 [M+Na]$^+$ (Calcd for C$_{25}$H$_{18}$F$_6$NaO$_6$S$_2$, 615.03467).

3) Synthesis of Intermediate Represented by Formula (b3)

The diol (14 mg, 0.024 mmol) of formula (a3) and bromotetraacetoglucose (97 mg, 0.24 mmol) were dissolved in CH$_2$Cl$_2$ (2 mL), and 0.1 g of molecular sieve 4 Å was added to the mixture to be agitated at room temperature for 1 hour. Ag$_2$O (56 mg, 0.24 mmol) was further added under an argon airflow at room temperature with the light blocked, then the mixture was agitated for 24 hours. After the reaction ended, the un-dissolved matter was filtered out under reduced pressure, the filtrate was decompressed/concentrated, and the residue was separated/refined by silica gel column chromatography (hexane:ethyl acetate=2:1 to 1:1) to obtain an intermediate represented by formula (b3) (16 mg, yield 64%) as a pale green amorphous.

The compound was subjected to mass analysis similarly to Example 1, and the peak was [M+Na]$^+$=1275. The peak comes from the target mass 1252, indicating the obtained compound is an intermediate represented by formula (b3).

ESI-MS m/z: 1275 [M+Na]$^+$.

HR-ESI-MS m/z: 1275.22742 [M+Na](Calcd for C$_{25}$H$_{18}$F$_6$NaO$_6$S$_2$, 1275.22483).

4) Synthesis of Compound of Formula (I-2) (Target Compound)

The intermediate (10 mg, 0.008 mmol) represented by formula (b3) is dissolved in methanol (2 mL), to which lithium hydroxide (3 mg, 0.08 mmol) was added at room temperature, then the mixture was agitated for 24 hours. After the reaction ended, the reaction solution was decompressed/concentrated, and the residue was separated/refined with Bio-Gel P-2 (H$_2$O) to obtain a reaction mixture. When the reaction mixture was mass analyzed, the peak was 917. The peak is derived from the target compound mass 916, indicating that the obtained compound is the compound of formula (I-2).

ESI-MS m/z: 917 [M+H]$^+$.

5) Analysis of Water Solubility

Figure 2:
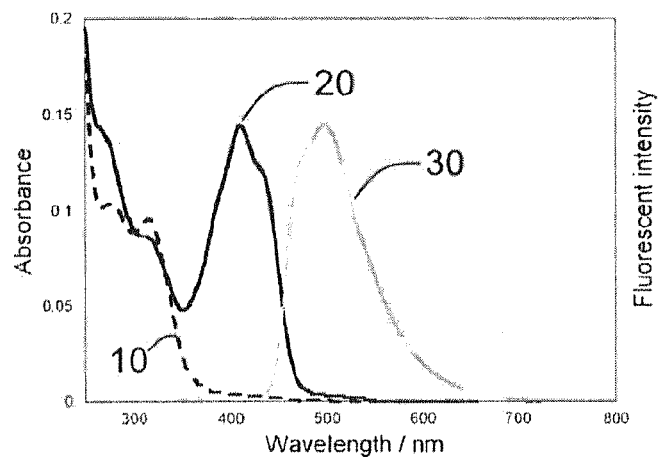
FIG. 2 is a diagram showing the photochromic property of an aqueous solution of a compound of Example 2.

The water solubility of a compound of formula (I-2) was assessed similarly to Example 1, to check that the compound is water soluble. Specifically, the compound of (1-2) was dissolved in a small amount of methanol (0.2 mL), and distilled water (4 mL) was added to prepare a 95% aqueous solution, and an absorption spectrum of FIG. 2 (by Hitachi, using U-4100) was obtained as a result. The spectrum of the open ring form is shown by dotted line 10. Irradiation with a UV light (313 nm) turned the solution yellow, and a spectrum shown by solid line 20 was observed. In addition, the irradiation with the UV light made the compound fluorescent, and a spectrum of solid line 30 was obtained.

Example 3

A Thiophene Compound (Second Production Method)

The reaction scheme is shown below.

[Formula 17]

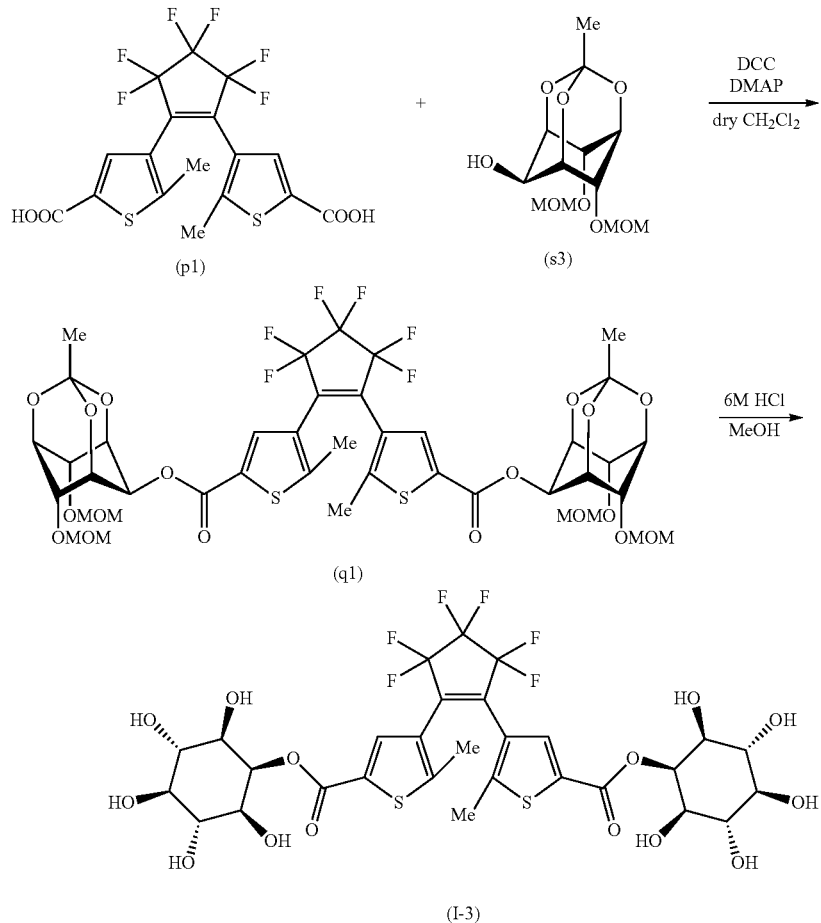

1) Synthesis of Protected Sugar

Synthesis of 2,4,6-Tri-O-benzoyl-Myo-Inositol 1,3,5-Orthoacetate (r1)

[Formula 18]

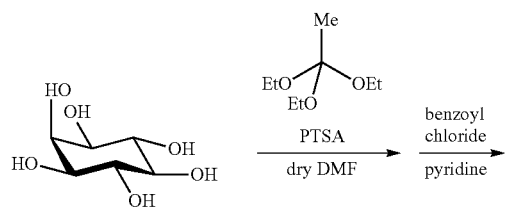

-continued

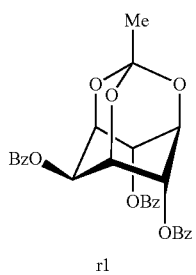

Myo-inositol (Tokyo Chemical Industry, 11.0 g, 61.1 mmol) and triethylorthoacetate (16.5 mL, 90.5 mmol) were added to dry DMF (80 mL). After reflux at 100° C. for 30 minutes, p-toluenesulfonic acid monohydrade (Tokyo Chemical Industry, 1.14 g, 5.99 mmol) was added after dissolution in dry DMF (10 mL). Then, reflux of the content per se was performed at 100° C. for 7.5 hours. The content temperature was readjusted to room temperature, trimethyl amine (Tokyo Chemical Industry, 4.0 mL, 28.9 mmol) was added, and the resulting material was agitated for 30 minutes. Further, benzene was added (10×2 mL), and the solvent was decompressed/removed. Then, pyridine (60 mL) was added. The content was cooled to 0° C., and benzoyl chloride (Tokyo Chemical Industry, 24.2 mL, 210 mmol) was dropped over a length of 1 hour. The content temperature was readjusted to room temperature, and the content was agitated for 16 hours. The content was recrystallized with methanol to produce a white solid compound r1 (21.2 g, 41.0 mmol, 67.1%). The results of the NMR (by JEOL Ltd., GSX400) and the mass analysis (Shimadzu Corporation, GCMS-QP2010) of the compound are as shown below.

$^1$H NMR (400 MHz, CDCl3): δ1.63 (s, 3H), 4.68-4.70 (m, 2H), 4.91-4.94 (m, 1H), 5.65 (m, 1H), 5.81 (m, 4H), 7.17-7.21 (m, 1H), 7.46-7.51 (m, 4H), 7.60-7.64 (m, 1H), 7.85-7.87 (m, 4H), 8.16-8.19 (m, 2H)

MS (FAB) m/z=516 [M]+

Synthesis of Myo-Inositol-1,3,5-Orthoacetate (r2)

[Formula 19]

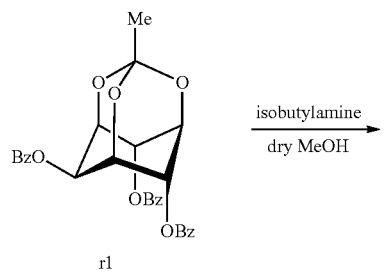

Under a nitrogen atmosphere, a compound of formula (r1) (18.0 g, 34.8 mmol), isobutylamine (Tokyo Chemical Industry, 14.0 mL, 49.9 mmol) were added to dry MeOH (60 mL) in the flask. Reflux of the content was performed at 65° C. for 24 hours. The solvent was decompressed/removed, and diethyl ether was added to the solvent, then the mixture was cooled in an ice bath. The resulting precipitation was filtered out under reduced pressure, and a compound r2 (6.16 g, 30.2 mmol; 86.7%) was obtained as a white powder. The analysis result was as shown below.

$^1$H NMR (400 MHz, CD$_3$OD): δ1.36 (s, 3H), 4.07-4.09 (m, 4H), 4.36-4.38 (m, 2H) MS (FAB) m/z=204 [M+]

Synthesis of 2-O-Tert-Butyldimethylsilyl-Myo-Inositol-1,3,5-Orthoacetate (r3)

[Formula 20]

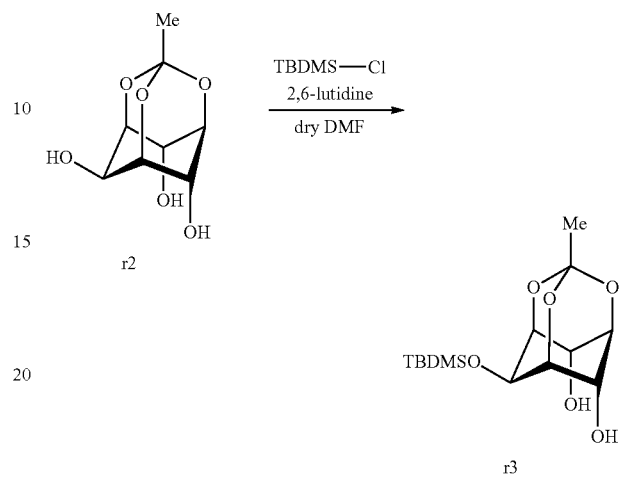

Under a nitrogen atmosphere, a compound of formula (r2) (3.26 g, 16.0 mmol), tert-butyldimethylchlorosilane (Tokyo Chemical Industry, 2.39 g, 15.9 mmol), 2,6-lutidine (Tokyo Chemical Industry, 5.0 mL, 42.9 mmol) were dissolved in the dry DMF (30 mL) in the flask. The content was agitated at room temperature for 36 hours. The solvent was decompressed/removed, and water (30 mL) was added. The solvent was cooled in an ice bath, and the resulting precipitate was filtered to obtain compound r3 (2.92 g, 9.17 mmol, 57.8%). The analysis result was as shown below.

$^1$H NMR (400 MHz, CDCl$_3$); δ0.15 (s, 6H), 0.95 (s, 9H), 1.45 (s, 3H), 4.14-4.16 (m, 2H), 4.18-4.20 (m, 1H), 4.21-4.23 (m, 1H), 4.52-4.54 (m, 2H)

MS (FAB) m/z=319 [M+1]$^+$

Synthesis of 2-O-Tert-Butyldimethylsilyl-4,6-Bis(O-Methoxymethyl)-Myo-Inositol-1,3,5-Orthoacetate (r4)

[Formula 21]

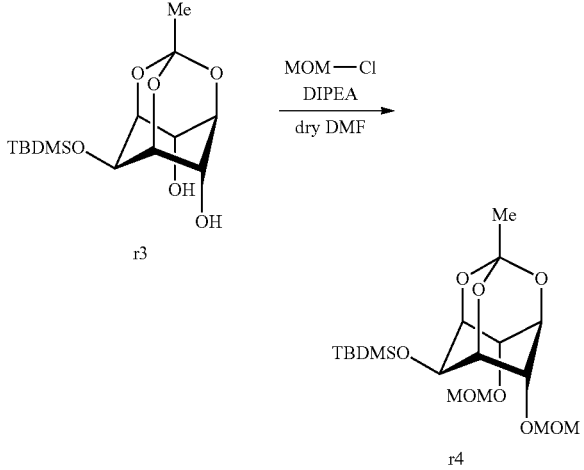

A compound of formula (r3) (1.77 g, 5.56 mmol) was dissolved in the dry DMF (30 mL) in a flask under a nitrogen atmosphere. N,N-Diisopropylethylamine (Tokyo Chemical Industry, 4.0 mL, 40.7 mmol) was added and methoxymethyl chloride (Tokyo Chemical Industry, 2.5 mL, 33.2 mmol) was dropped thereto. Reflux of the content was performed at 65° C. for 36 hours. The solvent was decompressed/removed, and extraction was performed using ethyl acetate. The resulting product was dried with magnesium sulfate, then a residue was refined by silica column chromatography (eluent; chloroform:methanol=8:1) to obtain compound r4 (1.69 g, 4.16 mmol, 74.8%). The analysis result was as shown below.

$^1$H NMR (400 MHz, CDCl$_3$); δ0.13 (s, 6H), 0.94 (s, 9H), 1.45 (s, 3H), 3.34 (s, 6H), 4.11-4.13 (m, 2H), 4.16-4.17 (t, J=2.0 Hz, 1H), 4.27-4.29 (m, 1H), 4.35-4.37 (m, 2H), 4.40-4.42 (m, 4H)

MS (FAB) m/z=407 [M+1]+

Synthesis of 4,6-Bis(O-Methoxymethyl)-Myo-Inositol-1,3,5-Orthoacetate (s3)

[Formula 22]

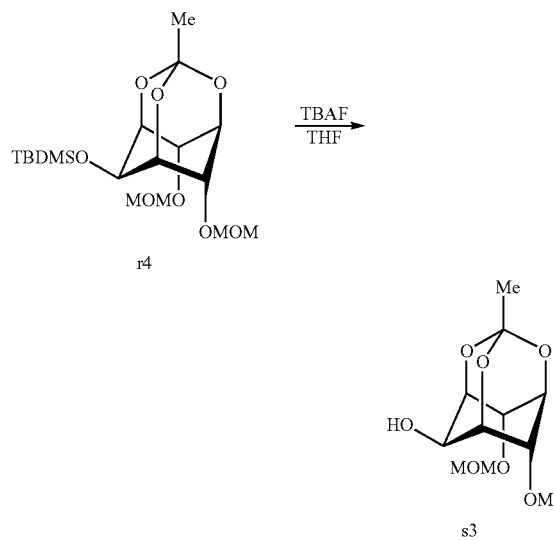

The compound of formula (r4) (1.59 g, 3.91 mmol) was dissolved in THF (15 mL) in the flask. Then, 1.0 mol/L of tetrabutylammonium fluoride (Tokyo Chemical Industry)-THF solution (5.1 mL, 5.1 mmol) was added and the mixture was agitated for 16 hours. The reaction was terminated with water (10 mL), then extraction was performed using diethylether, and drying was performed using magnesium sulfate. A residue was refined by silica gel column chromatography (eluent; hexane:ethyl acetate=6:1 to 4:1) to obtain compound s3 (0.82 g, 2.81 mmol, 71.8%). The analysis result was as shown below.

$^1$H NMR (400 MHz, CDCl$_3$); δ1.45 (s, 3H), 2.99 (d, J=12 Hz, 1H), 3.39 (s, 6H), 4.01-4.05 (m, 1H), 4.21-4.23 (m, 2H), 4.26-4.29 (m, 1H), 4.43 (t, J=3.8 Hz, 2H), 4.67-4.74 (m, 4H)

MS (FAB) m/z=293 [M+1]$^+$

2) Synthesis of Dicarboxylic Acids of Formula (p1)

Diformyls of formula (k1) were subjected to the following process to obtain dicarboxylic acids of formula (p1).

[Formula 23]

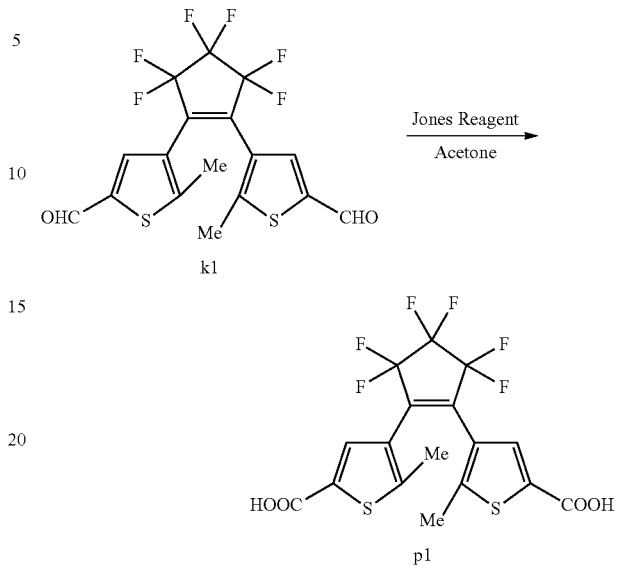

CrO$_3$ (3.19 g, 31.9 mmol) was dissolved in water (4.5 mL), and the solution was cooled with an ice bath, while concentrated sulfuric acid (3.0 mL) and water (9.0 mL) were added to prepare the Jones reagent. Then, the compound of formula (k1) (3.22 g, 7.59 mmol) was dissolved in acetone (80 mL) in the flask. The Jones reagent was dropped slowly in the flask, and the content of the flask was agitated for 17 hours. The reaction was terminated using 2-propanole (20 mL). Extraction was performed using diethylether, and drying was performed using magnesium sulfate. The solvent was decompressed/removed, and recrystallization was performed using ethyl acetate/hexane to obtain p1 (3.07 g, 6.73 mmol, 86.7%) as a white powder. The analysis result was as shown below.

1H NMR (400 MHz, CD3OD): 1.99 (s, 3H, Me), 7.72 (s, 1H, thienyl)

MS (EI) m/z=456 [M]+

3) Synthesis of Intermediate Represented by Formula (q1)

[Formula 24]

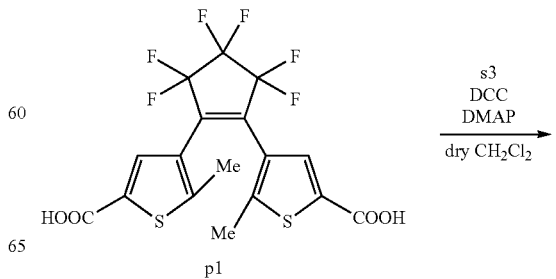

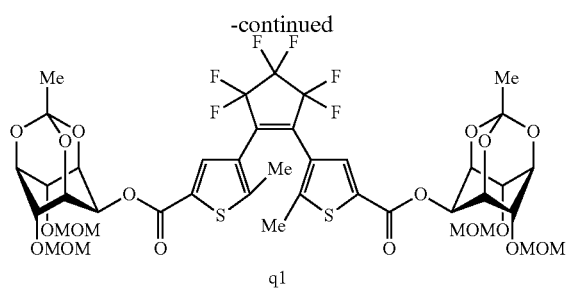

q1

Under a nitrogen atmosphere, the dicarboxylic acid of formula (p1) (320 mg, 0.701 mmol), N,N'-dicyclohexylcarbodiimide (0.415 mg, 2.01 mmol), 4-dimethylaminopyridine (30 mg, 0.246 mmol) were dissolved in dry $CH_2Cl_2$ (6 mL), and the mixture was agitated at room temperature for 30 minutes.

Then, the protected sugar of formula (s3) (480 mg, 1.64 mmol) was dissolved in dry $CH_2Cl_2$ (2 mL) to be added to the above solution, and agitated at room temperature over night. The generated solid was filtered under reduced pressure and washed with $CH_2Cl_2$. The solvent was decompressed/removed, and a residue was refined by silica gel column chromatography (eluent; dichloromethane:ethyl acetate=4:1) to obtain a pale yellow powder of an intermediate of formula (q1) (405 mg, 0.403 mmol, 58% yield). The results of NMR (by JEOL Ltd., GSX400) and mass analysis (Shimadzu Corporation, GCMS-QP2010) were as shown below. The analysis result was as shown below.

$^1$H NMR (400 MHz, CDCl$_3$): d 1.48 (s, 3H), 2.01 (s, 3H), 3.43 (s, 6H), 4.33 (sep, J=1.6 Hz, 1H), 4.42-4.43 (m, 2H), 4.46 (t, J=3.8 Hz, 2H), 4.71-4.78 (m, 4H), 5.43 (t, J=1.8 Hz, 1H), 7.83 (s, 1H)

MS (FAB) m/z=1004 [M$^+$]

4) Synthesis of Compound of Formula (I-3) (Target Compound)

The intermediate represented by formula (q1) (290 mg, 0.289 mmol) was dissolved in methanol (5 mL.). To the resulting solution, hydrochloric acid of 6 mol/L (25 mL) was added, and reflux of the solution was performed at 55° C. for 6 hours. Then, hydrogen chloride was trapped with sodium carbonate, while the solvent was decompressed/removed. The residue was refined by reversed-phase silica gel column chromatography (eluent; methanol:water=4:1) to obtain the compound of formula (I-3) (210 mg, 0.269 mmol, 93% yield). The analysis result was as shown below.

$^1$H NMR (400 MHz, CD$_3$OD): d 2.07 (s, 3H), 3.60-3.62 (m, 5H), 5.56 (s, 1H), 7.73 (s, 1H)

MS (FAB) m/z=780[M]$^+$

5) Analysis of Water Solubility

The water solubility of a compound of formula (I-3) was assessed in a similar manner as Example 1 to confirm that the compound is water soluble.

Figure 3:
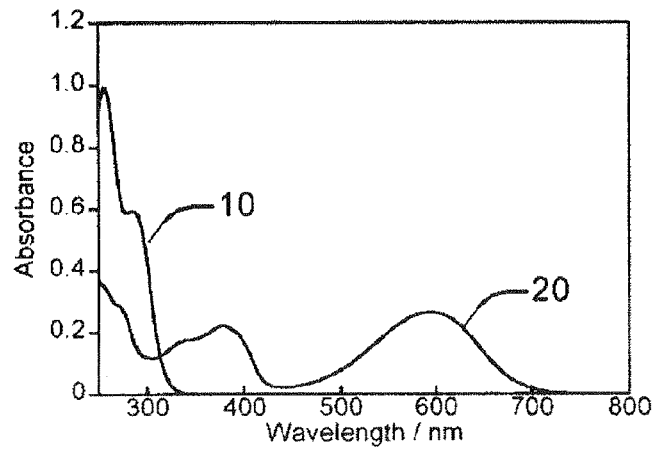
FIG. 3 is a diagram showing the photochromic property of an aqueous solution of a compound of Example 3.

The absorption spectrum (using U-4100 of Hitachi) of the aqueous solution thus obtained is shown in FIG. 3. Curve 10 is a spectrum of the compound (open ring form) of formula (I-3), and the maximum absorption wave length was 254 nm. Then, an aqueous solution of the compound of formula (I-3) was irradiated with light of 254 nm to obtain a photostationary state (PSS), in which the ring closing reaction has ended. The spectrum at this state is shown as curve 20. The maximum absorption wavelength of the closed ring form was 595 nm. The spectrum returned to the original spectrum upon irradiation with visible light longer than 600 nm indicating the reversible photochromism (the following scheme).

[Formula 25]

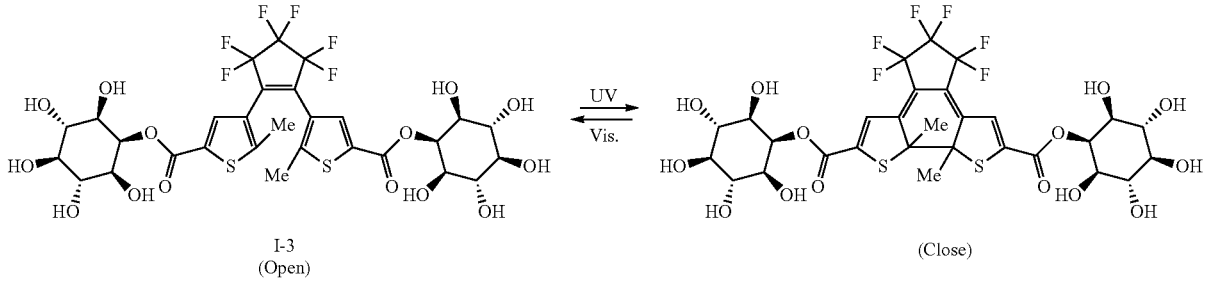

I-3
(Open)

(Close)

Example 4

Benzothiophene Sulfone Compound

The reaction scheme is shown below.

[Formula 26]

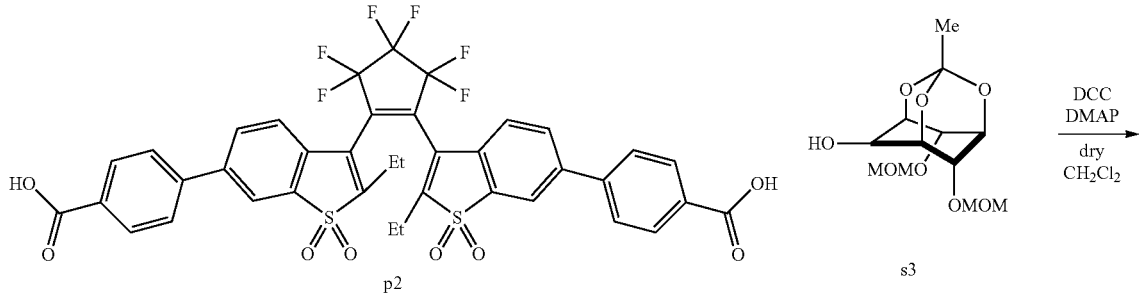

p2 s3

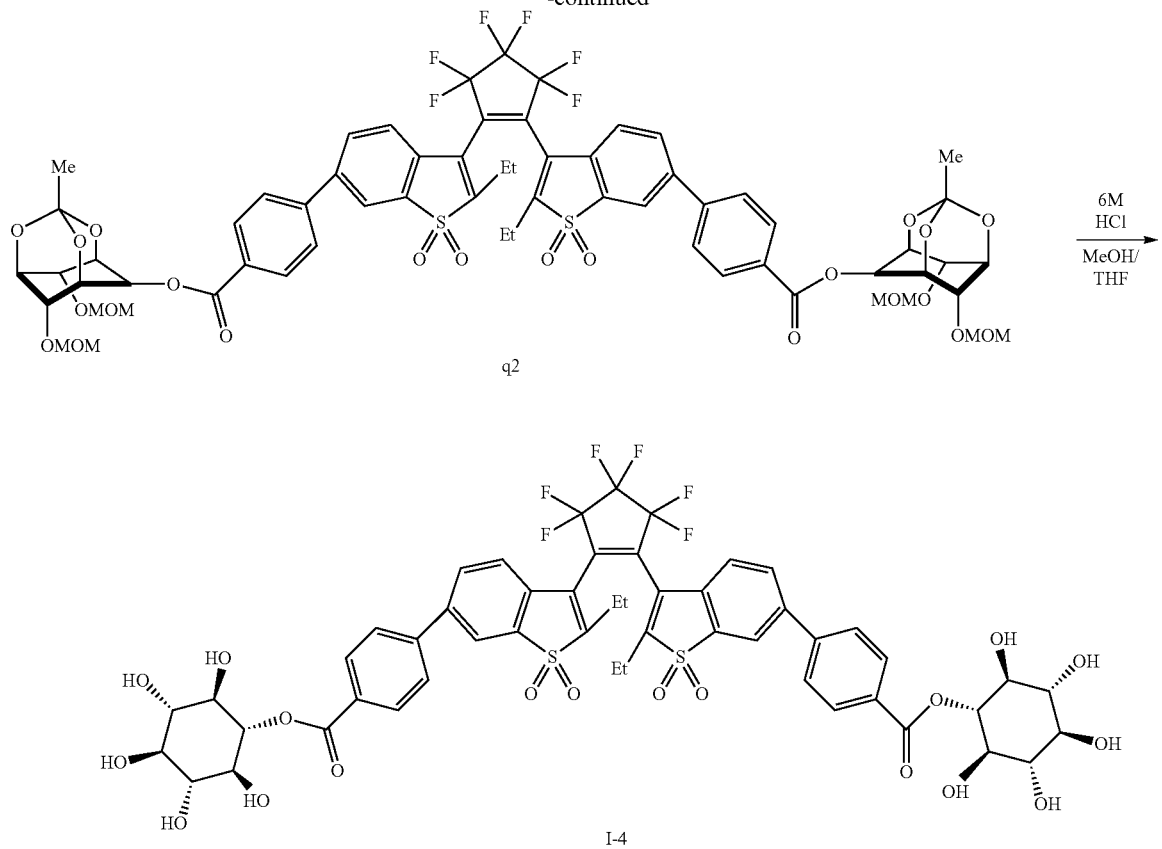
⓪ indicates text missing or illegible when filed
1) Synthesis of Dicarboxylic Acids of Formula (p2)
The reaction scheme is shown below.
[Formula 27]
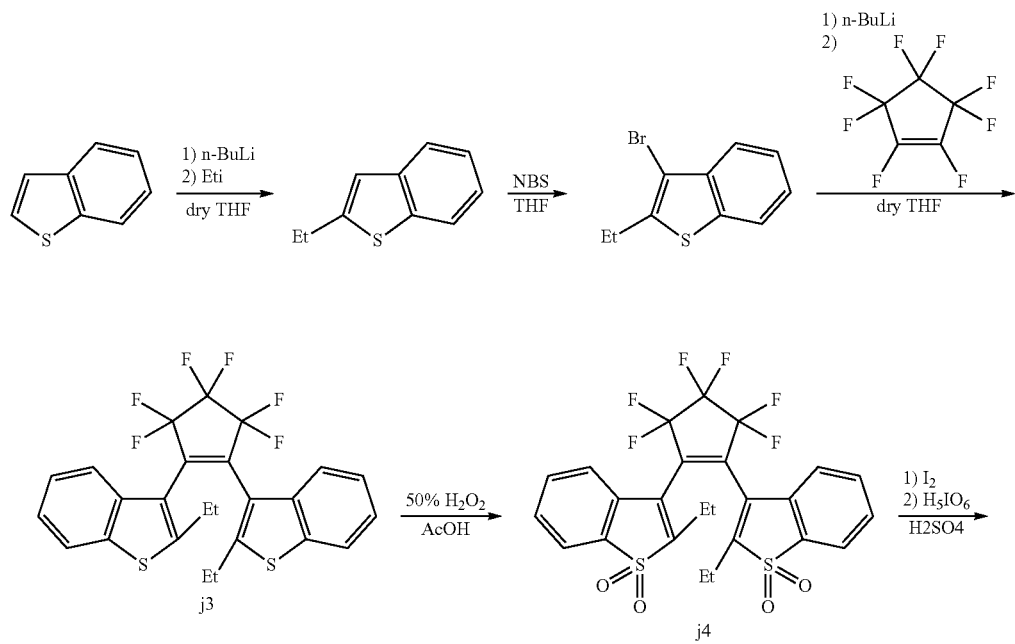

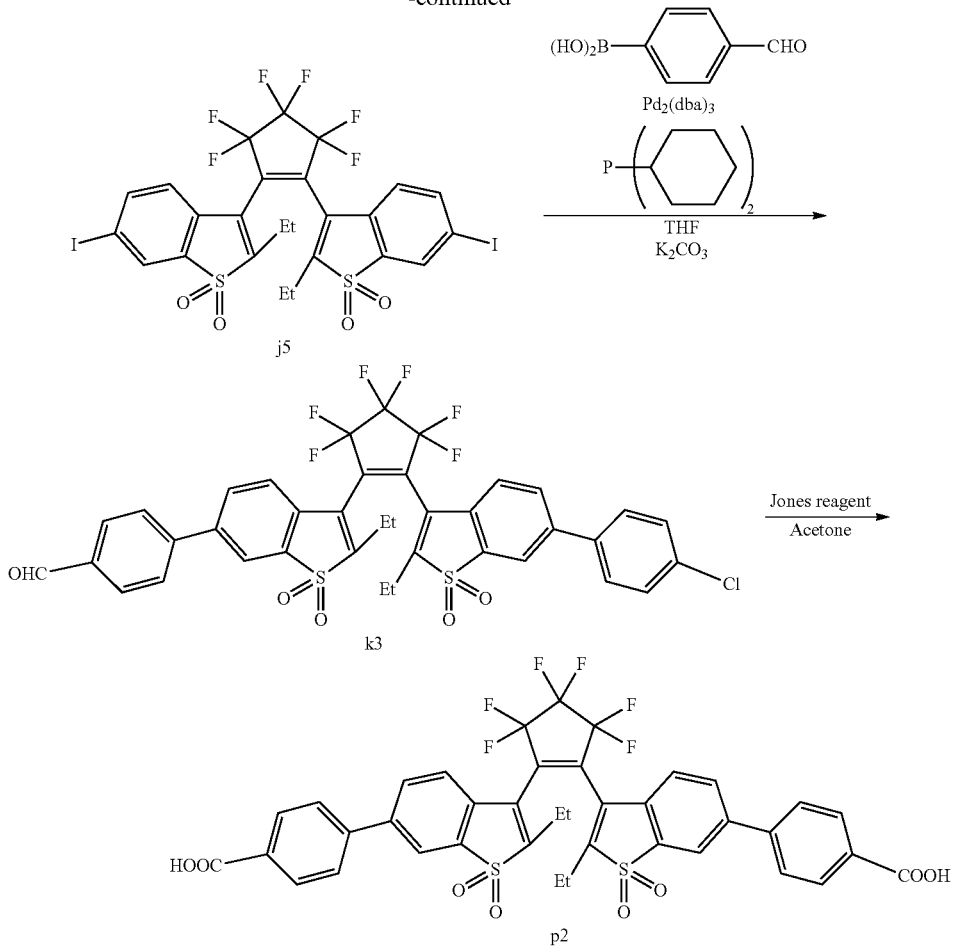

? indicates text missing or illegible when filed

The compound of formula (j3) was synthesized according to Non-Patent Document 6. The compound of formula (j4) was synthesized according to the synthesis method in 2) of Example 2. The compound of formula (j5) was synthesized by applying a common method using iodine and $H_5IO_6$ and introducing iodine in the compound of formula (j4)

The compound of formula (j5) (450 mg, 0.450 mmol) and 4-formylphenylboronic acid (199 mg, 1.33 mmol) were dissolved in THF (10 mL). Tris(dibenzylideneacetone)dipalladium (0) (95 mg, 0.104 mmol), potassium carbonate solution (10 mL), and an 18% toluene solution of tricyclohexylphosphine (0.1 mL) were added to the solution, then the resulting solution was agitated at room temperature for 20 minutes. The reaction product was treated with hydrochloric acid, then extraction was performed using chloroform. The extract was dried with magnesium sulfate, then the solvent was removed, and a residue was refined by silica gel column chromatography (eluent: hexane/ethyl acetate=4/1, 2/1) to obtain the compound of formula (k3). The yield amount was 353 mg (0.459 mmol), and the yield rate was 82.9%. The analysis result was as shown below.

MS (EI) m/z=768 [M+]

The compound of formula (k3) (200 mg, 0.260 mmol) was dissolved in acetone (10 mL) and an adjusted Jones reagent (0.6 mL, 1.17 mmol) was slowly dropped in the solution, then the solution was agitated overnight. The reaction was terminated using 2-propanol (2 mL), and the solvent was decompressed/removed. Extraction from the reaction product was performed using ethyl acetate, and the extract was dried with magnesium sulfate, then, the solvent was removed. Recrystallization was performed using ethyl acetate and hexane to obtain a compound of formula (p2). The yield amount was 122 mg (0.152 mmol) and the yield rate was 73.3%. The analysis result was as shown below.

MS (ESI) m/z=823.0865 [M+Na]+

2) Synthesis of Intermediate of Formula (q2)

The compound of formula (p2) (366 mg, 0.457 mmol), N,N-dicyclohexylcarbodiimide (283 mg, 1.37 mmol), 4-dimethylaminopyridine (19 mg, 0.152 mmol) were dissolved in dry dichloromethane (DCM) (12 mL) and agitated at room temperature for 30 minutes. A compound of formula (s3) (401 mg, 1.37 mmol), prepared in the above manner, was dissolved in dry dichloromethane (1 mL) to prepare a solution, then, the solution was added to a mixture containing the compound of formula (p2) and the resulting mixture was agitated overnight. The precipitation was removed by filtration under reduced pressure, and the solvent was decompressed/removed. A residue was refined by silica gel column chromatography (dichloromethane:ethyl acetate=4:1) to obtain a compound of formula (q2). The yield amount was 65 mg (0.048 mmol), and the yield rate was 11%. The analysis result was as shown below.

MS (ESI) m/z=1371.2971 [M+Na]+

3) Synthesis of Compound of Formula (I-4) (Target Compound)

The compound of formula (q2) (50 mg, 0.037 mmol) was dissolved in THF (1 mL), to which methanol (1 mL), and HCl of 6M (5 mL) were added. After 6 hours of reflux at 60° C., toluene (10 mL) was added, and the solvent was decompressed/removed. A residue was refined by reverse-phase column chromatography (methanol:water-4:1) to obtain the target compound. The analysis result was as shown below.

MS (ESI) m/z=1147.1922 [M+Na]$^+$

4) Analysis

Figure 4:
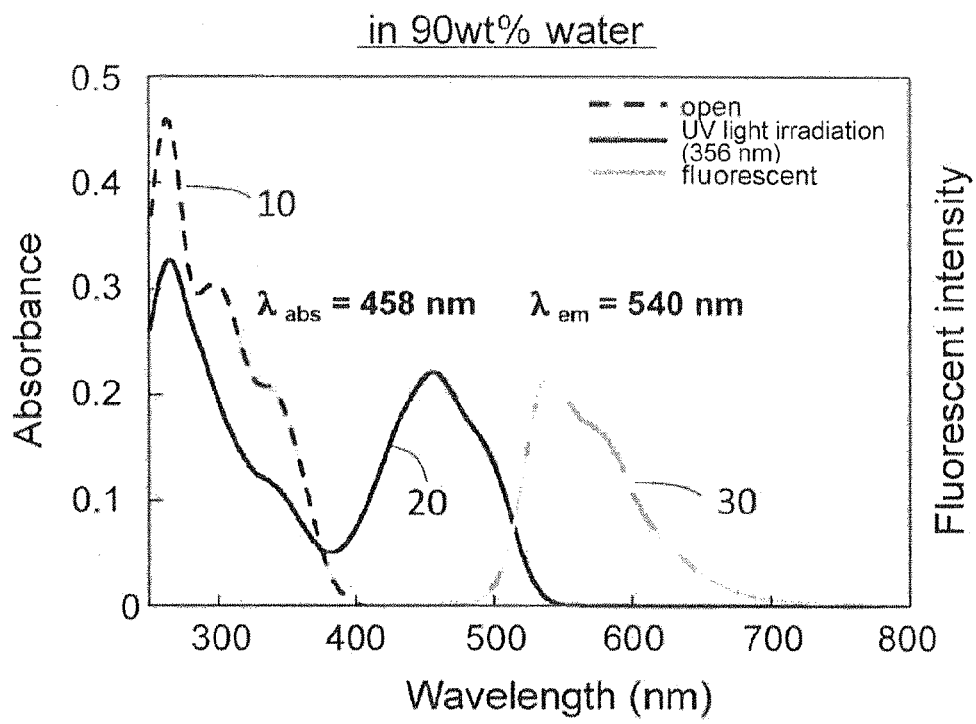
FIG. 4 is a diagram showing the photochromic property of an aqueous solution of a compound of Example 4.
Figure 5:
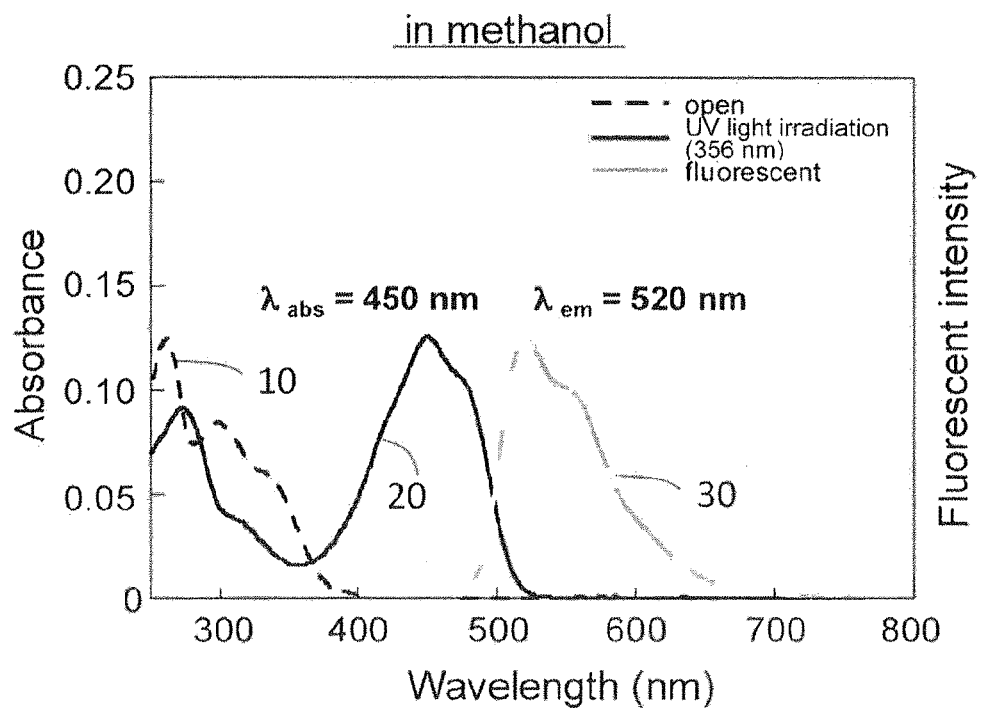
FIG. 5 is a diagram showing the photochromic property of a compound of Example 4 in methanol.

About 0.5 mg of the given compound was dissolved in each of 0.5 mL of water/methanol (weight rate of 90/10) and 0.5 mL of only methanol to prepare a solution. For convenience, the former will be referred to as an aqueous solution, and the latter will be referred to as a methanol solution. The absorption spectrum of the solutions are shown in FIGS. 4, 5. Curve 10 is a spectrum of the compound of formula (I-4) (open ring form). In the methanol solution, the maximum absorption wavelength is 450 nm, and the molar absorption coefficient was 39000 M$^{-1}$ cm$^{-1}$. The absorption disappeared when irradiated with visible light, and the solution returned to a colorless state. Curve 20 is a spectrum of the closed ring form. The closed ring form showed a light green fluorescence (curve 30), the fluorescence maximum was observed at 520 nm, and the fluorescent quantum yield was 0.71. Further, the fluorescence disappeared when the compound returned to the open ring form. It was thus shown that the compound of formula (I-4) shows reversible photochromism and switching of fluorescence in methanol.

In the aqueous solution, the maximum absorption wavelength of the open ring form was 458 nm, and the molar absorption coefficient was 36000 M$^{-1}$ cm$^{-1}$. The absorption disappeared when irradiated with visible light, and the solution returned to a colorless state. The closed ring form showed a yellow fluorescence (curve 30), the maximum luminescence was observed at 540 nm, and the fluorescent quantum yield was 0.44. Further, the fluorescence disappeared when the compound returned to the open ring form. It was thus shown that the compound of formula (I-4) shows reversible photochromism and switching of fluorescence in a mixed water/methanol (weight ratio of 90/10) solvent.

[Formula 28]

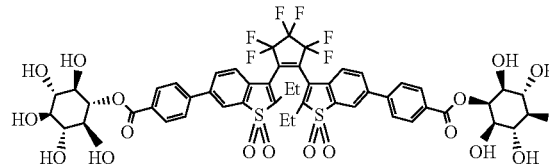

Example 5

Figure 6:
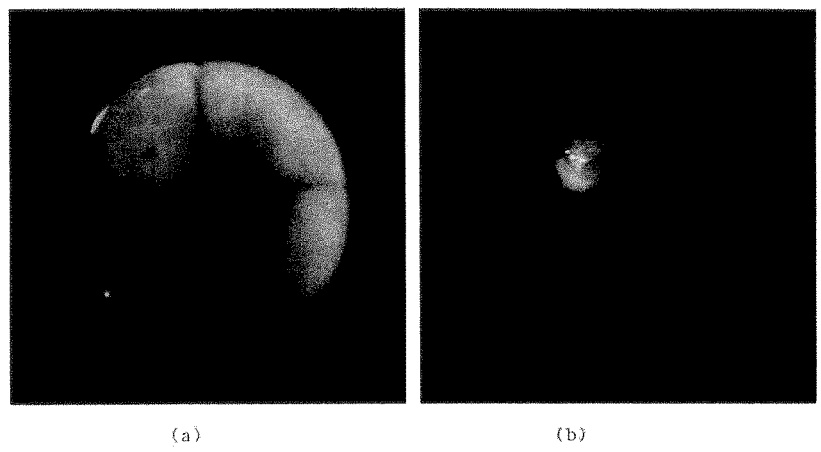
FIG. 6 is a diagram showing the fluorescent label property of a biological tissue.

About 0.5 mg of diarylethene of formula (I-4) was dissolved in 0.5 mL of methanol, to which water was added to prepare a water/methanol (weight ratio of 5/1) mixture. The solution was injected in the 4-cell stage embryo of a *Xenopus*. The state immediately after injection is shown in FIG. 6(*a*). The black spot at the upper left blastomere is the injection site. After injection, the cell was left untouched for about an hour to allow cell division (32-cell stage). The cells were irradiated with a UV light of 470 to 495 nm wavelength. Then, the cells were checked to see if there were any fluorescence, and fluorescence was confirmed around the injection site (FIG. 6 (*b*)).

Example 6

Figure 7:
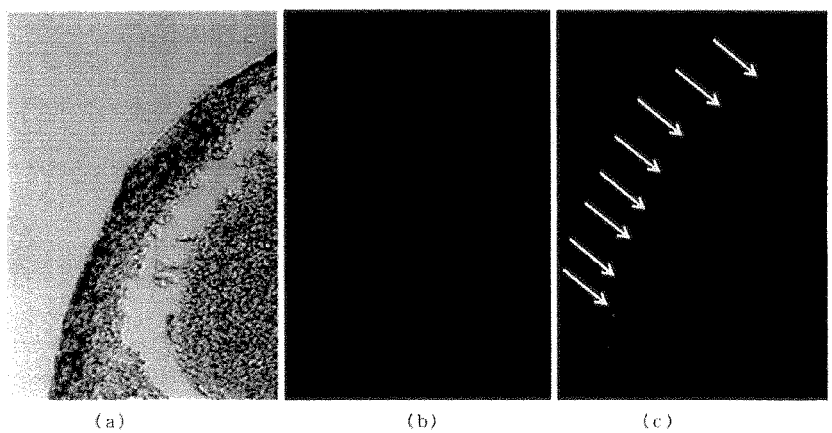
FIG. 7 is a diagram showing the fluorescent label property of a biological tissue

The solution prepared in Example 5 was placed on a 10 µm slice of tail-bud embryo head of a *Xenopus* and left untouched at room temperature for 30 minutes. Then, the tail-bud embryo head was washed with 10% methanol aqueous solution, and irradiated at a wavelength of 470-495 nm. Observation under bright field is shown in FIG. 7(*a*). The wavelength of 515 to 550 nm was detected under the dark field, but almost no light emission was seen as shown in FIG. 7(*b*). The subject was then irradiated with UV ray having a wavelength of 360 to 370 nm for 30 seconds, after which a wavelength of 515 to 550 nm was detected again (FIG. 7(*c*)). As shown in FIG. 7(*c*), the fluorescent signal was observed particularly on the outer layer of the epidermis of the embryo.

REFERENCE SIGNS LIST

10 Spectrum of open ring form
20 Spectrum of close ring form
30 Fluorescent spectrum

The invention claimed is:

1. A diarylethene compound represented by formula (I)

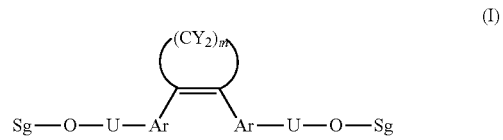

wherein, Sg is a monovalent sugar residue formed by removing one hydroxyl group from a sugar compound or a monovalent protected sugar residue formed by removing one hydroxyl groups from a sugar compound in which one or more other hydroxyl groups are protected, and wherein the sugar is selected from the group consisting of a six-membered ring sugar, a five-membered ring sugar, cyclitol and oligosaccharides containing a six-membered ring sugar, a five-membered ring sugar, or cyclitol;

U is —(CH$_2$)$_n$—, —CH$_2$—U'—, or —C(=O)—
wherein
n is an integer of 1 to 5,
U' is a C2-C10 branched alkylene group binding to Ar, and
Ar is a group represented by formula (A1) or (A2);

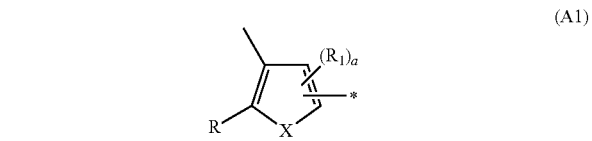

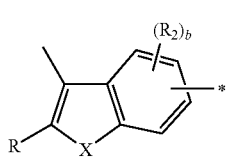

(A2)

wherein,
X is S, SO$_2$, NR$_3$ in which R$_3$ is a C1-C3 alkyl group, or O,
R is a C1-C4 alkyl group,
R$_1$ and R$_2$ are independently a C1-C3 alkyl group,
a is 0 or 1,
b is an integer of 0-3, and
* represents a bond with U;
Y is a hydrogen atom or a halogen atom; and
m is an integer of 3 to 5.

2. The compound according to claim 1, wherein the Sg is a monovalent sugar residue formed by removing one hydroxyl group from pyranose.

3. The compound according to claim 1, wherein the Sg is a monovalent sugar residue formed by removing one hydroxyl group from pyranose at a position-1 carbon.

4. The compound according to claim 1, wherein the Sg is a monovalent sugar residue formed by removing one hydroxyl group from cyclitol.

5. The compound according to claim 1, wherein the X is S or SO$_2$.

6. A method for producing a diarlyethene compound according to claim 1, comprising:

(1) a step of preparing a halogenated sugar derivative derived from a sugar-type compound selected from the group consisting of a six-membered ring sugar, a five-membered ring sugar, cyclitol and oligosaccharides containing a six-membered ring sugar, a five-membered ring sugar, or cyclitol, and having 1 hydroxyl group substituted with a halogen atom, and all other hydroxyl groups protected by protection groups;

(2) an etherification step of reacting the halogenated sugar derivative with the compound represented by formula (a) to generate a compound represented by formula (b)

[Formula 3]

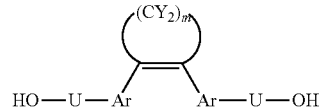

(a)

wherein, U, Ar, Y and m are as defined above;

[Formula 4]

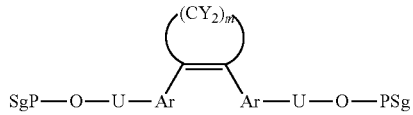

(b)

wherein, U, Ar, Y and m are as defined above, and PSg shows a group in which all hydroxyl groups of the Sg are protected; and (3) a deprotection step of removing a protection group of the compound represented by formula (b).

7. The method according to claim 6, wherein step (1) is performed under a presence of Ag$_2$O.

8. The method according to claim 6, wherein the halogen atom in the halogenated sugar derivative is bromine atom.

9. The method according to claim 6, wherein a protection group in the halogenated sugar derivative is an acyl group.

* * * * *